United States Patent [19]
Ishikura et al.

[11] Patent Number: 5,210,555
[45] Date of Patent: May 11, 1993

[54] OCULAR REFRACTING POWER MEASURING SYSTEM

[75] Inventors: Yasuhisa Ishikura; Ikuo Kitao, both of Tokyo, Japan

[73] Assignee: Kabushiki Kiasha TOPCON, Tokyo, Japan

[21] Appl. No.: 763,226

[22] Filed: Sep. 20, 1991

[30] Foreign Application Priority Data

Sep. 29, 1990 [JP] Japan .................... 2-262766

[51] Int. Cl.$^5$ ................... A61B 3/10; A61B 3/14
[52] U.S. Cl. ............................ 351/211; 351/214
[58] Field of Search ................. 351/211, 214, 221

[56] References Cited

U.S. PATENT DOCUMENTS 4,266,862 5/1981 Trotscher ..................... 351/211
4,929,076 5/1990 Musuda et al. ............. 351/211 X

FOREIGN PATENT DOCUMENTS 2-191428 11/1990 Japan .
3-23834 7/1991 Japan .

Primary Examiner—Rodney B. Bovernick
Attorney, Agent, or Firm—Nields & Lemack

[57] ABSTRACT

The ocular refracting power measuring system according to the present invention comprises a projector system having a measuring light source emitting light beam rotatable around optical axis and for projecting an image of light source of the measuring light source on retina of an eye to be tested, a light receiving system having a light blocking member for blocking a part of light beam reflected from retina of the eye to be tested by a circular edge and for conducting the light beam reflected from retina of the eye to be tested onto a photodetector placed at a position approximately conjugate with a pupil of the eye to be tested through said light blocking member, and a controller for calculating ocular refracting power based on the distribution of light amount on a meridian line on said photodetector corresponding to arbitrary position of the measuring light source and for calculating the astigmatic condition based on the ocular refracting power on a plurality of meridian lines.

8 Claims, 4 Drawing Sheets

OCULAR REFRACTING POWER MEASURING SYSTEM

BACKGROUND OF THE INVENTION

The present invention relates to an ocular refracting power measuring system, and in particular to an ocular refracting power measuring system, which can measure the astigmatic condition of the eye to be tested at the same time.

As traditional, an ocular refracting power measuring system of so-called photo-refraction type has been known. In the system the retina of the eye to be tested is illuminated by strobe light, the light beam condition on the pupil of the eye to be tested is taken by a camera, and the ocular refracting power of the eye to be tested as measured from these results.

However, in the system of the so-called photo-refraction type, a photograph is taken by an ordinary camera. As the result, the image on the photographed film must be analyzed and ocular refracting power must be calculated from the results of the analysis. Thus, it is not possible to obtain the measurement results with high accuracy. Or, the measurement is made after developing the film, and this means that it is impossible to obtain the measurement results at an instant.

Further, the measurement for astigmatism such as the degree of astigmatism, the angle of astigmatism, etc. has not been taken into account in this conventional type system. Therefore, the measurement for astigmatism must be performed by another measuring system.

By the Japanese Provisional Patent Publication No. 191428/1990, the present applicant proposed an ocular refracting power measuring system, which can measure ocular refracting power with high accuracy and instantaneously according to the distribution of light amount. By this system, the image of light source is projected on retina of the eye to be tested, and the light beam from light source reflected at the retina is blocked by an edge-like light blocking member. The light beam thus blocked is received by a light receiving element, and the ocular refracting power is measured based on the distribution of light amount in the light beam.

The present invention is to offer an ocular refracting power measuring system, which is based on the invention previously applied and which can also measure the degree of astigmatism, the angle of astigmatic axis, etc.

DETAILED DESCRIPTION OF THE PREFERRED EMBODIMENT

In the following, an embodiment of the present invention will be described in connection with the drawings.

In the ocular refracting power measuring system according to a previous Japanese patent application (Japanese Provisional Patent Publication No. 191428/1990), light beam from the light source reflected at retina is blocked by an edge-like light blocking member, and the light beam thus blocked is received by a light receiving element, and the ocular refracting power is measured based on the result of the receiving condition on the light receiving element. In case the blocked light beam is received by light receiving element, the distribution of light amount on the light receiving element corresponds to the ocular refracting power and in perpendicular direction against edge line (meridian line direction) due to the influence of blocking. Meanwhile, astigmatism occurs because of the difference in ocular refracting power (diopter) on each meridian line, and the condition of astigmatism is defined by the spherical curvature S, the degree of astigmatism C, and the angle of astigmatic axis A. Here, the relationship between diopter $D\theta$ and the spherical curvature S, the degree of astigmatism C, the angle of astigmatic axis A on meridian line at arbitrary angle $\theta$ can be given by the following formula:

$$D\theta = S + C \sin(\theta - A) \qquad (1)$$

Therefore, if the values of diopter on meridian lines of $\theta_1$, $\theta_2$ and $\theta_3$ are known, the spherical curvature S, the degree of astigmatism C and the angle astigmatic axis A can be obtained. This allows to define the condition of astigmatism.

Figure 1:
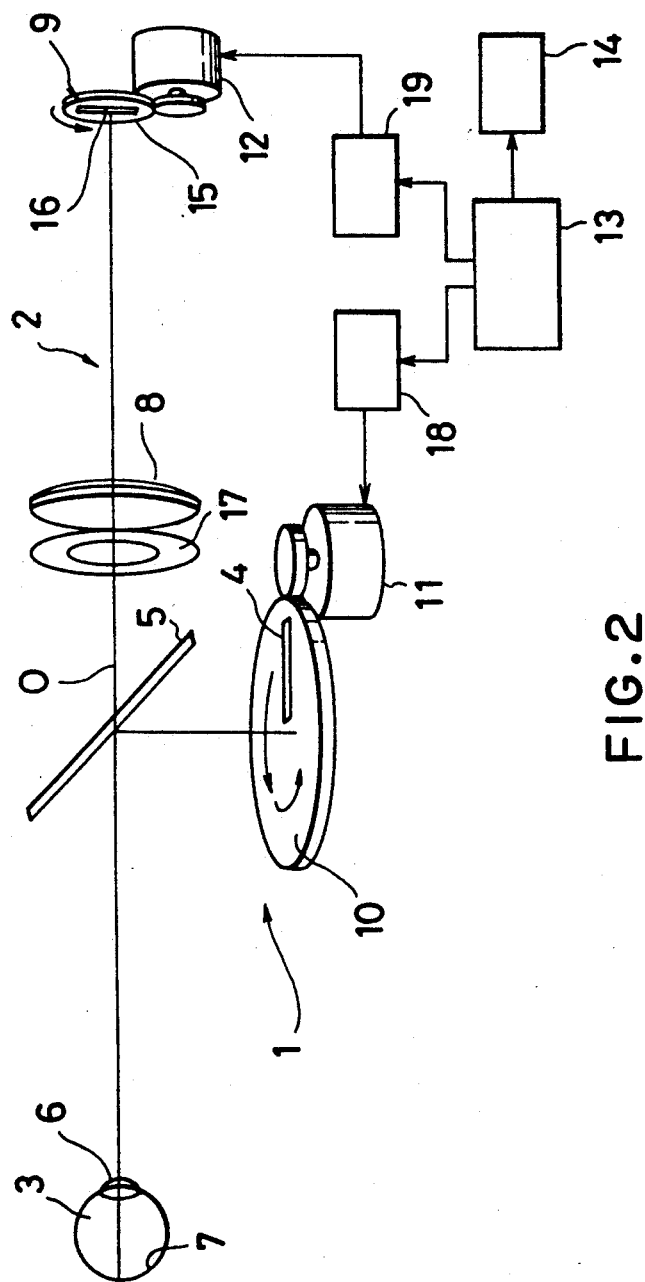
FIG. 1 is a basic configuration of an embodiment of the present invention.
Figure 2:
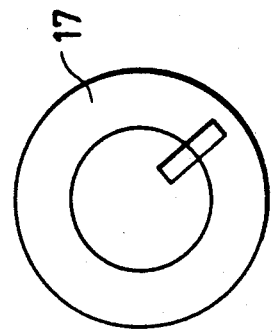
FIG. 2 is a drawing for explaining the relationship between light blocking member and light beam.

FIG. 1 gives approximate configuration of the present embodiment.

In the figure, 1 represents a projector system for projecting the image of the measuring light source on the retina 7 of the eye to be tested 3, and 2 is a light receiving system for receiving the light beam reflected from the retina 7. The projector system 1 and the light receiving system 2 are placed at face-to-face position to the eye to be tested 3.

The projector system 1 comprises a very fine slit-like measuring light source 4 installed on the radius of a disk 10 which can be rotated around the optical axis of the projector system, and a half-mirror 5 for reflecting the light beam from said measuring light source 4 toward the eye to be tested. The disk 10 is rotated by a motor 11 for light source.

Further, the projector system 1 projects the light beam from the measuring light source 4 in such manner that the image of the measuring light source 4 is formed on the retina 7 through the pupil 6.

The light receiving system 2 comprises an objective lens 8 and a photodetector (light receiver) 9, and the light beam reflected from the retina 7 is conducted onto the photodetector 9 through the half-mirror 5.

The photodetector 9 comprises a light receiving plate 15 rotatably mounted around the optical axis of the light receiving system and a line sensor 16 installed on diameter of the light receiving plate 15, and the light receiving plate 15 is rotated by a motor 12 for the photodetector.

The line sensor 16 is disposed in conjugated position with the pupil 6 of the eye to be tested about the objective lens 8.

In the optical path of the light receiving system, a light blocking member 17 is provided within the plane perpendicular to the optical axis 0 and at the position where the image of the measuring light source is formed when the ocular refracting power of the eye to be tested 3 is the standard diopter. The light blocking member 17 is a doughnut-shaped plate which has inner peripheral margin in edge form.

The light blocking member 17 blocks a part of the reflected light beam from the retina of the eye to be tested.

The motor 11 for light source and the motor 12 for photodetector are driven by motor drivers 18 and 19, and the driving instruction signal from a controller 13 is inputted to each of these two drivers 18 and 19. Both motors 11 and 12 are synchronously driven by the controller 13.

The photodetector 9 is connected to the controller 13, and the signal from the photodetector 9, i.e. the signal with line sensor 16 in light receiving state is inputted to the controller 13. The controller 13 memorizes the light receiving condition of the line sensor 16 and calculates ocular refracting power from the light receiving condition and the astigmatic condition from ocular refracting power on a plurality of meridian lines, thereby outputting the results to the display unit 14 as appropriate.

In the following, description will be given on the operation.

As described above, the measurement of astigmatism is performed by measuring ocular refracting power (diopter) on 3 meridian lines. Measurement is performed by projecting the measuring light beam from said very fine slit-like measuring light source 4 on the retina of the eye to be tested and by blocking a part of reflected light beam from the retina of the eye to be tested by means of the light blocking member 12. The reflected light beam, a part of which has been blocked by the light blocking member, is projected on the photodetector 9. The position of the slit-like measuring light source 4 is controlled in such manner that the direction of the line sensor 16 of the photodetector 9 concurs with the reflected light beam in slit-like form.

The line sensor 16 inputs the light receiving condition of the reflected light beam thus projected to the controller 13. The reflected light beam thus projected is blocked by the light blocking member 12, and the lightness is gradually increased or decreased in perpendicular direction (meridian direction) in relation to the edge on the photodetector. The degree of this increase or decrease, i.e. the gradient of the distribution of light amount of the received light beam represents the ocular refracting power, and the increasing or decreasing direction depends upon whether the ocular refracting power of the eye to be tested is bigger or smaller than the standard diopter.

The controller 13 measures the ocular refracting power based on the signal from line sensor 16.

According to the Japanese Provisional Patent Publication No. 191428/1990, the deviation $\Delta D$ of diopter is given by:

$$\Delta D = \alpha L D_0 / \mu$$

where $\alpha$ is the gradient of the distribution of light amount, $D_0$ the standard diopter, $\mu$ the diameter of pupil, and L the size of the light source. Thus, the diameter of the pupil is needed for calculation. To eliminate the influence of individual difference in pupil diameter, it is preferable to install a diaphragm (not shown) of a certain form smaller than the pupil diameter of any eye to be tested at the conjugated position of the eye to be tested on the projected side and light receiving side, or at least on the projected side.

In this case, if the diaphragm is placed only on the projected side, only the data on the site corresponding to the diaphragm on the projected side of the light receiving plate 15 of the photodetector should be processed.

In case it is necessary to compensate the aberration of the eye to be tested by pupil diameter, the compensation value corresponding to each of pupil diameters may be added. Or, a changeover switch may be used (not shown). Or, only the data on the region in a certain proportion to the pupil diameter of the eye to be tested may be used for calculation.

When the measurement in one meridian direction is completed, the motor 11 for light source and the motor 12 for photodetector are rotated synchronously by the angle required, and the ocular refracting power of the other meridian direction is measured. Further, the motor 11 for light source and the motor 12 for photodetector are rotated synchronously, and ocular refracting power on the third meridian line is measured.

For taking the signals of the light receiving condition of the line sensor 16 on each of the meridian lines, the disk 10 and the photodetector 14 may be intermittently driven, or they may be synchronously rotated, and the signals at three predetermined angles may be taken.

From the results of the measurement of ocular refracting power at least on 3 meridian lines, the spherical curvature S, the degree of astigmatism C, and the angle of astigmatic axis A can be obtained promptly by the above equation (I).

As described above, it is possible according to the present invention to easily measure the ocular refracting power on an arbitrary plurality of meridian lines and to measure the condition of astigmatic condition simultaneously with the measurement of ocular refracting power of the eye to be tested.

The measuring accuracy can be improved by measuring the ocular refracting power at two points varying by 180° on a meridian line and by averaging the results.

Figure 3:
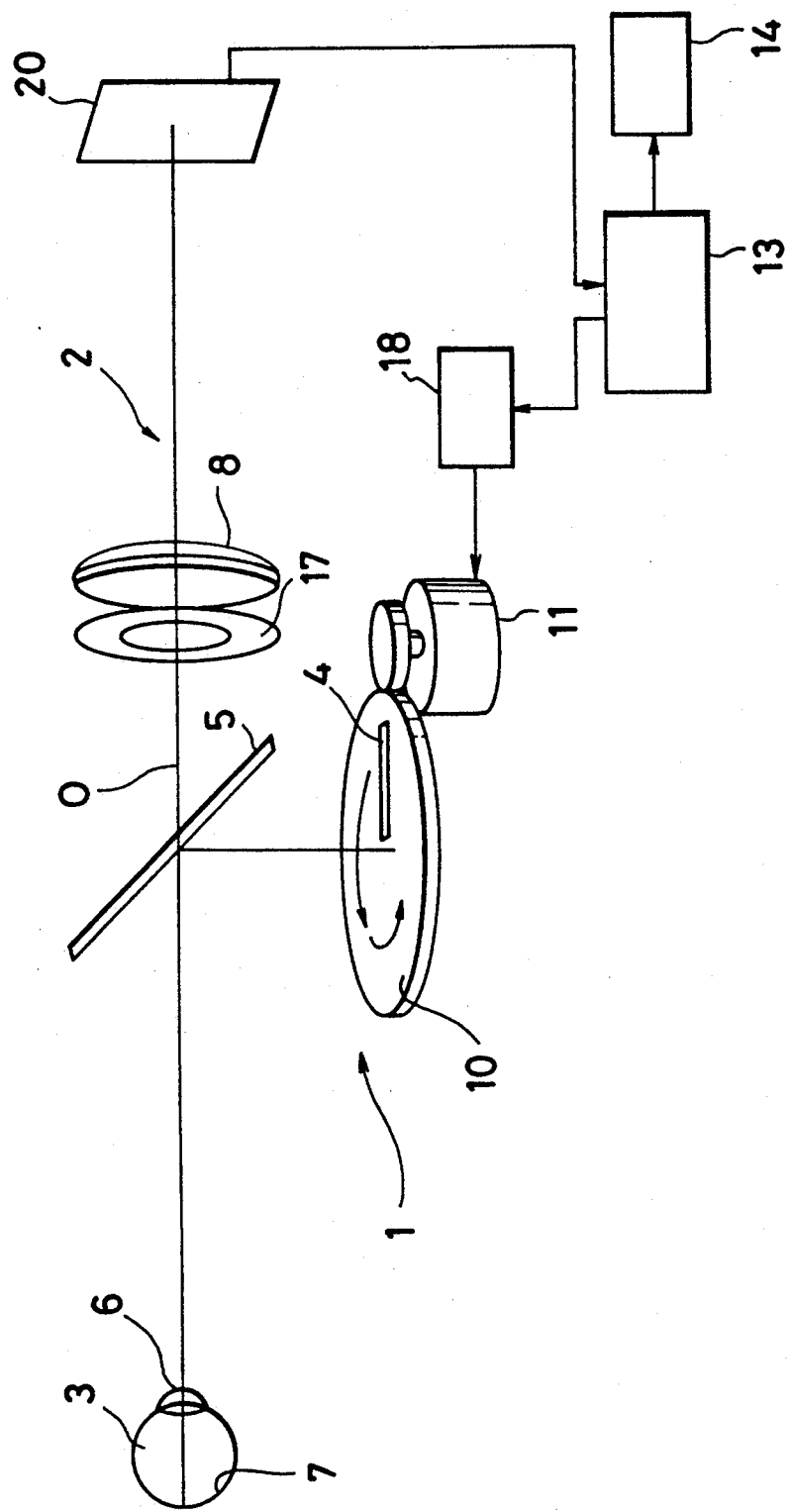
FIG. 3 is a basic configuration of another embodiment of this invention.

In the above embodiment, a line sensor is used, whereas planar light receiving element 20 consisted of CCD may be used as shown in FIG. 3, and the rotating mechanism of the photodetector may be eliminated.

Figure 4:
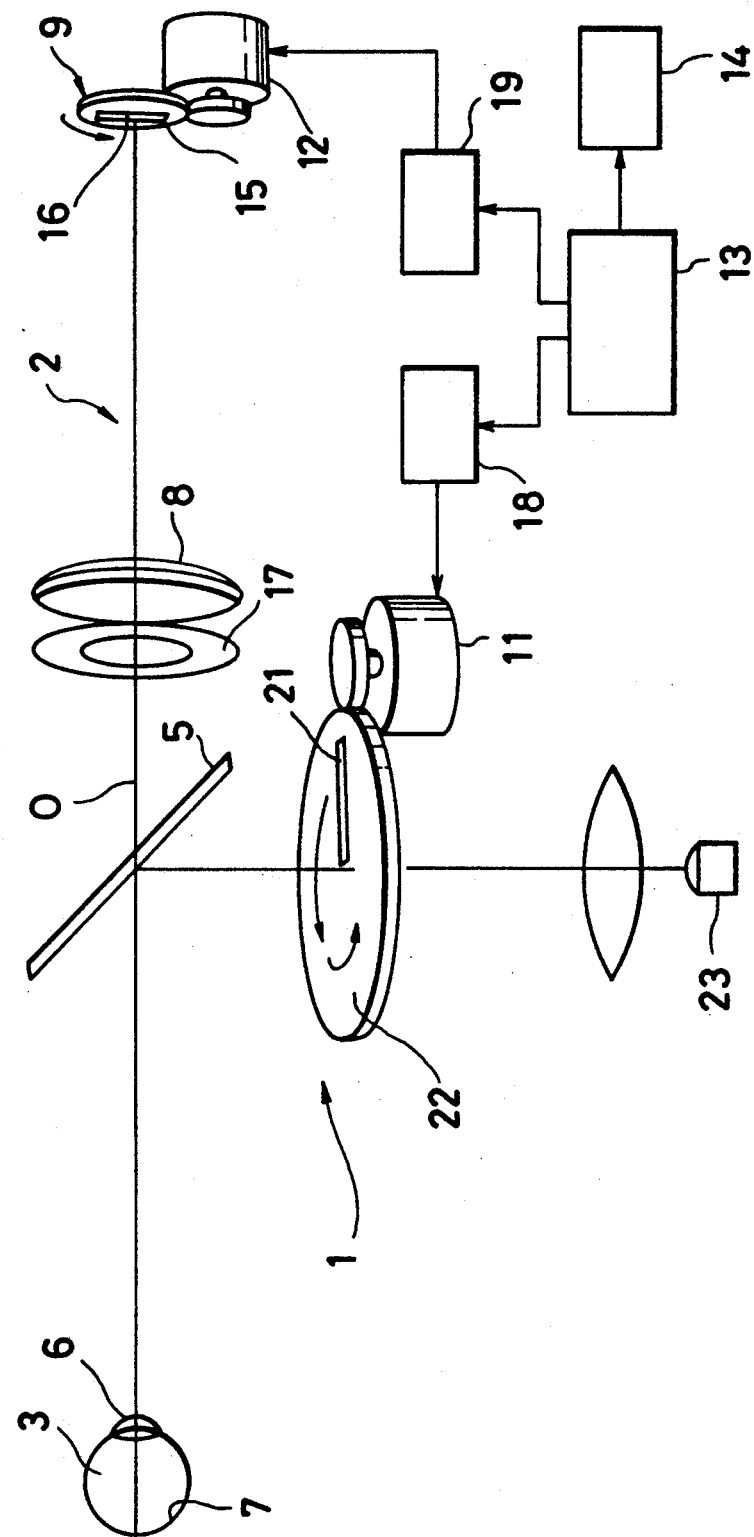
FIG. 4 is a basic configuration of still another embodiment of this invention.

As shown in FIG. 4, a diaphragm 22 having a very fine slit 21 may be placed, instead of the slit-like light source 4, at conjugated position with the eye to be tested 3, and slit-like measuring light may be irradiated to the eye to be tested through the slit 21 by the light source 23 separately furnished. In this case, a diaphragm 22 have some slits and liquid crystal material may be used for the slits, and the portion corresponding to the slit can be sequentially changed over.

For the astigmatic measurement, the spherical curvature S, the degree of astigmatism C, and the angle of astigmatic axis A can be obtained from the image data in 2 meridian lines according to the previous application of the present applicant (Japanese Patent Application No. 160083/1989).

Figure 5:
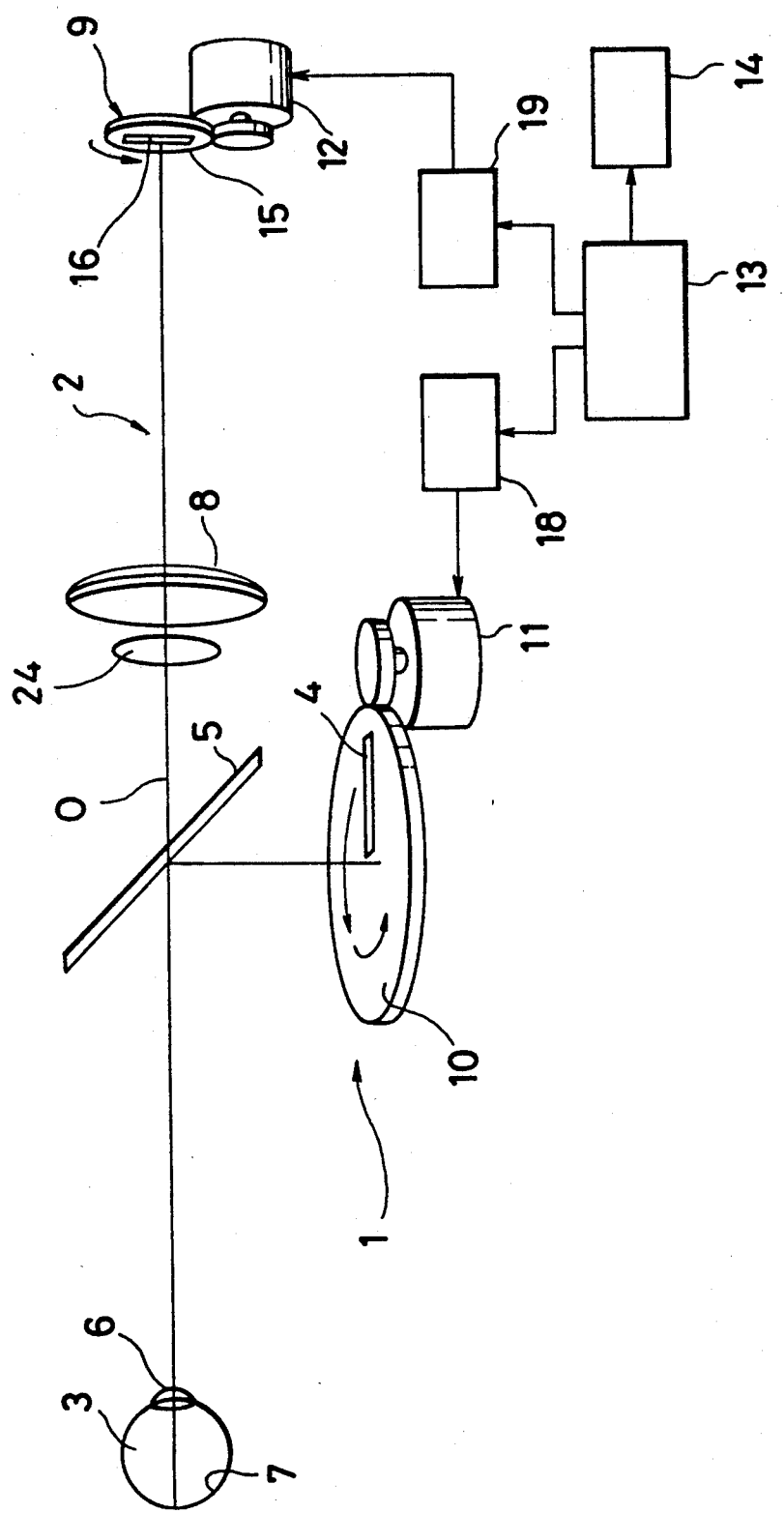
FIG. 5 is a basic configuration of yet still another embodiment of this invention.

Further, in the above embodiment, outer portion of the light beam is blocked by the light blocking member in form of a hollow doughnut, whereas the inner side of the slit-like light beam may be blocked by a solid disk 24 as shown in FIG. 5.

What is claimed is:

1. An ocular refracting power measuring system, comprising a projector system having a measuring light source emitting light beam rotatable around optical axis and for projecting an image of light source of said measuring light source on retina of an eye to be tested, a light receiving system having a fixed light blocking member for blocking a part of light beam reflected from retina of said eye to be tested by a circular edge whose center is in correspondence with the optical axis of said light receiving system, defining meridian lines at right angles thereto and having a photodetector capable of measuring the distribution of light amount along a line and being placed at a position approximately conjugate with a pupil of said eye to be tested through said fixed light blocking member, whereby said light beam reflected from retina of said eye to be tested impinges onto said photodetector, said photodetector having a plurality of meridian lines thereon, and a controller adapted to calculate ocular refracting power based on the distribution of light amount on a meridian line at right angles to said circular edge on said photodetector corresponding to arbitrary position of said measuring light source and to calculate the astigmatic condition based on said ocular refracting power on a plurality of meridian lines.

2. An ocular refracting power measuring system according to claim 1, wherein said light blocking member is in form of doughnut.

3. An ocular refracting power measuring system according to claim 1, wherein said light blocking member is in form of disk.

4. An ocular refracting power measuring system according to claim 1, wherein the projector system projects slit-like light beam.

5. An ocular refracting power measuring system according to claim 4, wherein said measuring light source is in form of slit.

6. An ocular refracting power measuring system according to claim 4, wherein there is provided a slit-like diaphragm to turn the light beam from the measuring light source to slit-like light beam.

7. An ocular refracting power measuring system according to claim 4, wherein the light receiving element is a planar light receiving element.

8. An ocular refracting power measuring system, comprising a projector system having a measuring light source emitting light beam rotatable around optical axis and for projecting an image of light source of said measuring light source on retina of an eye to be tested, a light receiving system having a fixed light blocking member for blocking a part of light beam reflected from retina of said eye to be tested by a circular edge whose center is in correspondence with the optical axis of said light receiving system defining meridian lines at right angles thereto and having a photodetector capable of measuring the distribution of light amount along a line and being placed at a position approximately conjugate with a pupil of said eye to be tested through said fixed light blocking member, whereby said light beam reflected from retina of said eye to be tested impinges onto said photodetector, said photodetector having a plurality of meridian lines thereon, and a controller adapted to calculate ocular refracting power based on the distribution of light amount on a meridian line at right angles to said circular edge on said photodetector corresponding to arbitrary position of said measuring light source and to calculate the astigmatic condition based on said ocular refracting power on a plurality of meridian lines, wherein the projector system projects slit-like light beam, and wherein the light receiving element is a line sensor and is synchronously rotated with the measuring light source.

* * * * *

UNITED STATES PATENT AND TRADEMARK OFFICE
CERTIFICATE OF CORRECTION

PATENT NO. : 5,210,555
DATED : May 11, 1993
INVENTOR(S) : Yasuhisa Ishikura and Ikuo Kitao It is certified that error appears in the above-identified patent and that said Letters Patent is hereby corrected as shown below:

On the title page:

Item "[73] Assignee: Kabushiki Kiasha TOPCON, Tokyo, Japan" should read

--[73] Assignee: Kabushiki Kaisha TOPCON, Tokyo, Japan--

Signed and Sealed this

Twenty-first Day of December, 1993

Attest:

BRUCE LEHMAN

Attesting Officer     Commissioner of Patents and Trademarks